(12) United States Patent
Worthen

(10) Patent No.: US 6,554,797 B1
(45) Date of Patent: Apr. 29, 2003

(54) METHOD AND SYSTEM FOR PATIENT TEMPERATURE MANAGEMENT AND CENTRAL VENOUS ACCESS

(75) Inventor: William J. Worthen, Coto de Caza, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 09/815,612

(22) Filed: Mar. 23, 2001

Related U.S. Application Data

(63) Continuation-in-part of application No. 09/253,109, filed on Feb. 19, 1999.

(51) Int. Cl.[7] .................................................. A61F 7/12
(52) U.S. Cl. ........................ 604/113; 606/21; 607/106
(58) Field of Search ................................ 604/113, 507, 604/508, 509, 93.01, 114, 174, 175, 179, 180, 523; 607/104, 105, 106, 21, 23; 606/21–26

(56) References Cited

U.S. PATENT DOCUMENTS

| | | | |
|---|---|---|---|
| 4,164,943 A | * 8/1979 | Hill et al. .............. | 128/DIG. 26 |
| 4,820,349 A | 4/1989 | Saab ........................... | 128/344 |
| 5,246,421 A | 9/1993 | Saab ........................... | 604/96 |
| 5,264,260 A | 11/1993 | Saab ........................... | 428/35.5 |
| 5,337,734 A | 8/1994 | Saab ........................... | 128/4 |
| 5,342,301 A | 8/1994 | Saab ........................... | 604/96 |
| 5,358,486 A | 10/1994 | Saab ........................... | 604/96 |
| 5,411,477 A | 5/1995 | Saab ........................... | 604/96 |
| 5,443,781 A | 8/1995 | Saab ........................... | 264/291 |
| 5,499,973 A | 3/1996 | Saab ........................... | 604/96 |
| 5,569,195 A | 10/1996 | Saab ........................... | 604/96 |
| 5,624,392 A | 4/1997 | Saab ........................... | 604/43 |
| 5,755,690 A | 5/1998 | Saab ........................... | 604/96 |
| 5,837,003 A | 11/1998 | Ginsburg ..................... | 607/106 |
| 5,879,329 A | 3/1999 | Ginsburg ..................... | 604/93 |
| 5,902,268 A | 5/1999 | Saab ........................... | 604/96 |

(List continued on next page.)

FOREIGN PATENT DOCUMENTS

| | | | |
|---|---|---|---|
| EP | 0 274 411 A2 | 7/1988 | .......... A61M/29/02 |
| EP | 0 304 258 A3 | 2/1989 | .......... A61B/17/22 |
| EP | 0 457 456 A1 | 11/1991 | .......... A61M/25/00 |
| WO | WO 91/17788 | 11/1991 | .......... A61M/29/00 |
| WO | WO 96/07448 | 3/1996 | .......... A61M/29/00 |
| WO | WO 98/26831 | 6/1998 | .......... A61M/25/00 |
| WO | WO 98/31312 | 7/1998 | ............ A61F/7/12 |
| WO | WO 00/10494 | 3/2000 | ............ A61F/7/00 |
| WO | WO 00/38601 | 7/2000 | ............ A61F/7/00 |
| WO | WO 00/47145 | 8/2000 | ............ A61F/7/00 |
| WO | WO 00/48670 | 8/2000 | ............ A61N/1/30 |
| WO | WO 00/51534 | 9/2000 | ............ A61F/7/00 |
| WO | WO 00/53135 | 9/2000 | ............ A61F/7/00 |
| WO | WO 00/57823 | 10/2000 | ............ A61F/7/12 |
| WO | WO 00/62837 A3 | 10/2000 | .......... A61B/18/04 |
| WO | WO 00/66053 | 11/2000 | ............ A61F/7/12 |
| WO | WO 00/72779 A2 | 12/2000 | |
| WO | WO 00/72787 A1 | 12/2000 | ............ A61F/7/12 |
| WO | WO 01/03606 A2 | 1/2001 | |
| WO | WO 01/08580 A1 | 2/2001 | |
| WO | WO 01/10323 A1 | 2/2001 | .......... A61B/19/00 |
| WO | WO 01/10365 A1 | 2/2001 | ............ A61F/7/00 |
| WO | WO 01/12061 A1 | 2/2001 | .......... A61B/5/00 |
| WO | WO 01/12122 A2 | 2/2001 | |
| WO | WO 01/13809 A1 | 3/2001 | .......... A61B/18/18 |
| WO | WO 01/13837 A1 | 3/2001 | ............ A61F/7/00 |
| WO | WO 01/17471 A1 | 3/2001 | ............ A61F/7/12 |
| WO | WO 01/19447 A1 | 3/2001 | .......... A61M/31/00 |
| WO | WO 01/26590 A1 | 4/2001 | ............ A61F/7/12 |
| WO | WO 01/30413 A2 | 5/2001 | |

Primary Examiner—Michael J. Hayes
Assistant Examiner—Catherine Serke
(74) Attorney, Agent, or Firm—John L. Rogitz

(57) ABSTRACT

A catheter with metal heat exchange elements communicating with a source of coolant in a closed loop for effecting patient temperature control and at least two infusion lumens for providing access to the central venous blood supply when the catheter is placed in the central venous system. An anchor can be provided to suture or tape the catheter to the skin of a patient.

8 Claims, 1 Drawing Sheet

U.S. PATENT DOCUMENTS

| | | | |
|---|---|---|---|
| 5,989,238 A | 11/1999 | Ginsburg | 604/500 |
| 6,004,289 A | 12/1999 | Saab | 604/96 |
| 6,019,783 A | 2/2000 | Philips et al. | 607/105 |
| 6,042,559 A | 3/2000 | Dobak, III | 604/7 |
| 6,096,068 A * | 8/2000 | Dobak et al. | 606/21 |
| 6,110,168 A | 8/2000 | Ginsburg | 606/27 |
| 6,126,684 A | 10/2000 | Gobin et al. | 607/113 |
| 6,146,411 A | 11/2000 | Noda et al. | 607/105 |
| 6,149,670 A | 11/2000 | Worthen et al. | 607/3 |
| 6,149,673 A | 11/2000 | Ginsburg | 607/96 |
| 6,149,676 A | 11/2000 | Ginsburg | 607/106 |
| 6,149,677 A | 11/2000 | Dobak, III | 607/106 |
| 6,165,207 A | 12/2000 | Balding et al. | 607/105 |
| 6,224,624 B1 * | 5/2001 | Lasheras et al. | 607/105 |
| 6,231,594 B1 | 5/2001 | Dae | 607/96 |
| 6,231,595 B1 | 5/2001 | Dobak, III | 607/106 |
| 6,235,048 B1 | 5/2001 | Dobak, III | 607/104 |
| 6,238,428 B1 | 5/2001 | Werneth et al. | 607/105 |
| 6,245,095 B1 | 6/2001 | Dobak, III et al. | 607/105 |
| 6,251,129 B1 | 6/2001 | Dobak, III et al. | 607/105 |
| 6,251,130 B1 | 6/2001 | Dobak, III et al. | 607/105 |
| 6,299,599 B1 * | 10/2001 | Pham et al. | 604/101.03 |

* cited by examiner

METHOD AND SYSTEM FOR PATIENT TEMPERATURE MANAGEMENT AND CENTRAL VENOUS ACCESS

RELATED APPLICATIONS

This is a continuation-in-part of co-pending U.S. patent application Ser. No. 09/253,109, filed Feb. 19, 1999, incorporated herein by reference.

FIELD OF THE INVENTION

The present invention relates to methods and systems for patient temperature management.

BACKGROUND

It has been discovered that the medical outcome for a patient suffering from severe brain trauma or from ischemia caused by stroke or heart attack is improved if the patient is cooled below normal body temperature (38° C.). Furthermore, it is also accepted that for such patients, it is important to prevent hyperthermia (fever) even if it is decided not to induce hypothermia.

As recognized by the present invention, the above-mentioned advantages in regulating temperature can be realized by cooling the patient's entire body. Moreover, the present invention understands that since many patients already are intubated with central venous catheters for other clinically approved purposes anyway such as drug delivery and blood monitoring, providing a central venous catheter that can also cool the blood requires no additional surgical procedures for those patients. A cooling central venous catheter is disclosed in the above-referenced parent application.

Another cooling catheter is disclosed in U.S. Pat. No. 6,096,068. Unfortunately, the '068 invention does not recognize the above-noted desirability of combining conventional central venous line functions with a temperature regulation function. The present invention, however, makes this critical observation and provides the solutions set forth herein.

SUMMARY OF THE INVENTION

A central venous access catheter includes first and second elongated segments, with each segment having a turbulence-inducing irregular exterior surface. A flexible articulating joint connects the first and second elongated segments. Also, a tubular conduit is disposed substantially coaxially within the first and second elongated, articulated segments. The conduit has a fluid supply lumen for transporting a pressurized working fluid to a distal end of the elongated, articulated segments. The catheter also defines at least two infusion lumens separated from the working fluid and terminating in respective ports longitudinally separated from each other. Accordingly, each infusion lumen provides a means for accessing the central venous blood supply of a patient when the catheter is placed in the central venous system of a patient. An anchor can be located proximal to at least one elongated segment and configured for affixing the catheter to the skin of a patient.

In another aspect, a central venous catheter includes at least first and second hollow metal heat exchange elements. Each element has an outer surface that is configured for inducing turbulence in a fluid flowing past the surface. A closed circuit fluid pathway conveys coolant to and from the heat exchange elements.

In one implementation, at least first and second infusion lumens separated from the coolant terminate in respective ports that are longitudinally separated from each other. Each infusion lumen provides a means for accessing the central venous blood supply of a patient when the catheter is placed in the central venous system of a patient. In another implementation, an anchor is located proximal to at least one heat exchange element and is configured for affixing the catheter to the skin of a patient.

In still another aspect, a method for treating a patient includes advancing a catheter into the central venous system of the patient, and circulating a heat exchange fluid through the catheter to exchange heat with the patient. Simultaneously with the circulating act, at least one central venous (CV) line function is undertaken.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
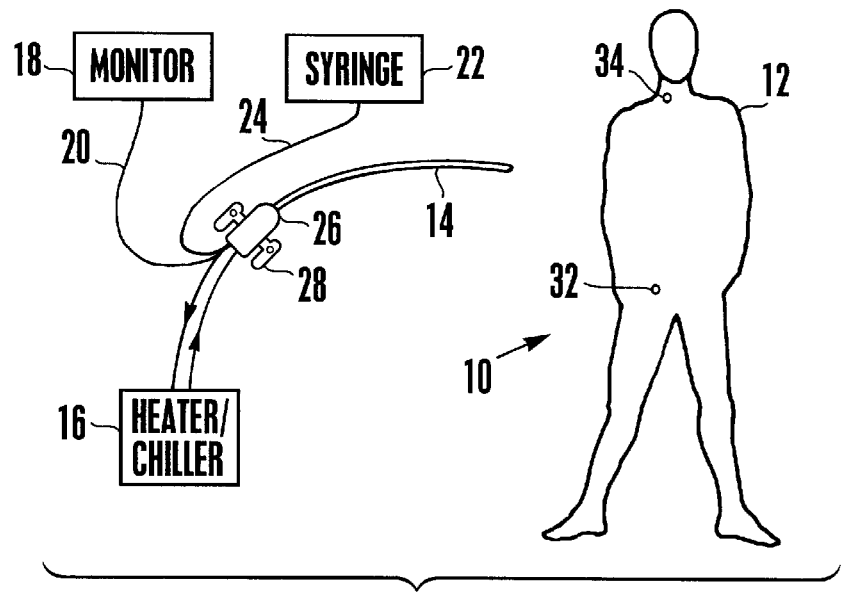
FIG. 1 is a schematic view of one intended environment of the central venous access catheter.

Referring initially to FIG. 1, a system, generally designated 10, is shown for managing and otherwise controlling patient temperature while providing access to the central venous system of a patient 12. As shown, the system 10 includes a central venous access and heat exchange catheter 14 that receives a heat exchange fluid (also referred to herein as "coolant") from a heater/chiller 16, with the fluid circulating in a closed loop. The fluid can be saline or other fluid such as refrigerant. Either the fluid flow rate and/or the temperature of the fluid is controlled by a controller associated with the heater/chiller 16 based on a patient temperature feedback signal to control the amount and if desired the rate at which heat is added or subtracted from the patient. The controller can be implemented by a software-executing processor or by discrete logic circuits or other electronic circuitry device to establish a desired patient temperature by appropriately controlling the flow rate and/or heat exchanger in response to a temperature signal derived from a sensor in the patient 12.

As also shown in FIG. 1, at least two central venous (CV) components can be in communication with the catheter 16 for undertaking central venous functions in addition to controlling the temperature of the patient. These functions include and are not limited to drug infusion and blood extraction for blood monitoring, as well as blood pressure monitoring. For instance, a blood monitor 18 can communicate with the catheter 14 via a line 20 to monitor blood pressure or withdraw blood from the central venous system of the patient 12. Also, a syringe 22 can engage the catheter 14 via a connector 24 for infusing drugs or other medicament such as epinephrine into the patient 12. The components 16, 18, 22 can all be connected to the catheter 14 via a proximal connector hub 26 of the catheter 14. The hub 26 can be formed with a suture anchor 28 or other anchor structure such as tape for providing a means to fasten the catheter 14 to the skin of the patient 14 for long-term use.

Figure 2:
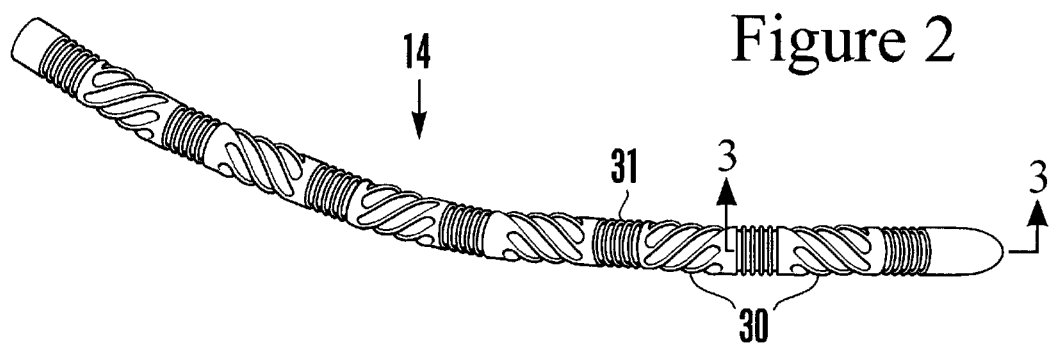
FIG. 2 is a perspective view of the central venous access catheter.

As shown in FIG. 2, the catheter 14 can include plural heat exchange elements 30. The heat exchange elements 30 can be established by one or more metal, preferably gold, hollow elongated segments that have external surfaces which have turbulence-inducing irregular exterior surfaces that are shaped to induce gentle turbulence in blood flowing past the elements. Separating adjacent heat exchange elements 30 can be a flexible articulating joint 31, it being understood that the heat exchange elements 30 and joints 31 can be formed from a single piece of material such as plastic or metal, e.g., gold. The details of the heat exchange elements 30 and their configuration are set forth in U.S. Pat. No. 6,096,068, incorporated herein by reference. In any case, coolant is circulated in a closed fluid communication loop between the heat exchange elements 30 and heater/chiller 16 to remove heat from the patient 12 or to add heat to the patient to rewarm the patient after surgery or after the termination of therapeutic hypothermia treatment.

Referring back to FIG. 1, the catheter 14 is advanced (possibly through an introducer sheath) into the vena cava of the patient 12 through a groin entry point 32 or through a neck entry point 34 to the central venous system of the patient 12. When advanced through the groin the catheter is advanced either through the saphenous vein or femoral vein to the inferior vena cava, and when advanced through the neck through the jugular or subclavian vein to the superior vena cava or inferior vena cava.

Figure 3:
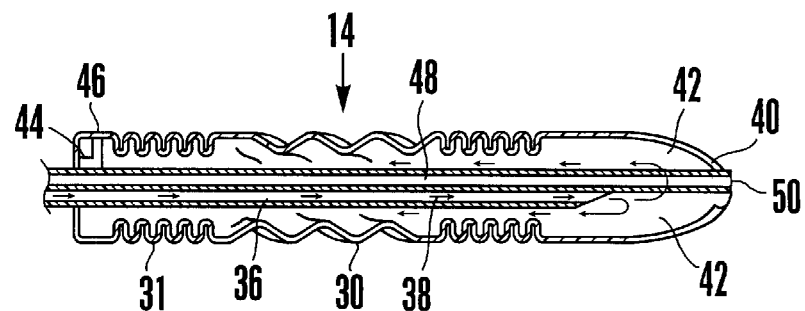
FIG. 3 is a cross-sectional view as seen along the line 3—3 in FIG. 2.

Now referring to FIG. 3, it can be seen that the catheter 14 establishes a tubular conduit that is disposed substantially coaxially within the heat exchange elements 30, with the conduit having a supply lumen 36 for supplying a pressurized working fluid (represented by arrows 38) to a distal end 40 of the catheter 14. As the fluid exits the supply lumen 38, it flows out and around the supply lumen 38 in a proximal direction as shown in an annular return lumen 42. It may readily be appreciated that heat is exchanged between the fluid 38 and bloodstream into which the catheter 14 is placed across the walls of the heat exchange elements 30 to heat or cool the patient as desired.

In addition to the supply and return lumens 36, 42, the catheter 14 has at least two and possibly more infusion or working lumens (only two shown for clarity) for undertaking CV functions simultaneously with controlling patient temperature. Specifically, as shown in FIG. 3, a first infusion or working lumen 44 terminates in a first outlet port 46, and a second infusion or working lumen 48 terminates in a second outlet port 50. Both lumens 44, 48 are separated from the fluid 38 and both lumens 44, 48 preferably extend to the hub 26 shown in FIG. 1. The second infusion or working lumen 48 can be coaxial with the body of the catheter 14 as shown. The second port 50 can be located on the distal tip of the catheter 14 as shown. In any case, to provide for mixing of infused drugs in the bloodstream if two drugs are to be administered, the ports 46, 50 are longitudinally separated from each other as shown. With the above in mind, the monitor 18 (FIG. 1) or other CV device such as an infusion device can communicate with one of the infusion or working lumens 44, 48 while the syringe 22 can communicate with the other infusion or working lumen 48, 44.

While the particular METHOD AND SYSTEM FOR PATIENT TEMPERATURE REGULATION AND CENTRAL VENOUS ACCESS as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. ?112, sixth paragraph, unless the element is expressly recited using the phrase "means for".

What is claimed is:

1. A central venous access catheter, comprising:

first and second elongated segments, each segment having a turbulence-inducing irregular exterior surface;

a flexible articulating joint connecting the first and second elongated segments;

a tubular conduit disposed substantially coaxially within the first and second elongated segments, the conduit having a fluid supply lumen for transporting a pressurized working fluid to a distal end of the elongated, articulated segments; and the catheter also defining at least two infusion lumens separated from the working fluid and terminating in respective ports longitudinally separated from each other, each infusion lumen providing access to the central venous blood supply of a patient when the catheter is placed in the central venous system of a patient.

2. The catheter of claim 1, further comprising an anchor located proximal to at least one elongated segment and configured for affixing the catheter to the skin of a patient.

3. A central venous catheter, comprising:

at least first and second hollow metal heat exchange elements, each having an outer surface configured for inducing turbulence in a fluid flowing past the surface;

at least one closed circuit fluid pathway for conveying coolant to and from the heat exchange elements; and at least first and second infusion lumens separated from the coolant and terminating in respective ports longitudinally separated from each other, each infusion lumen providing access to the central venous blood supply of a patient when the catheter is placed in the central venous system of a patient.

4. The catheter of claim 3, further comprising an anchor located proximal to at least one heat exchange element and configured for affixing the catheter to the skin of a patient.

5. A method for treating a patient, comprising:

advancing a catheter into the central venous system of the patient;

circulating a heat exchange fluid through the catheter to exchange heat with the patient; and simultaneously with the circulating act, undertaking one or more central venous (CV) line functions, wherein the catheter has at least one heat exchange element made of metal and having an exterior surface adapted to create turbulence in blood flowing past the surface.

6. The method of claim 5, wherein the CV function is medicament infusion.

7. The method of claim 5, wherein the CV function is blood monitoring.

8. The method of claim 5, comprising undertaking at least two CV functions.

* * * * *